(12) United States Patent
Sobie

(10) Patent No.: US 10,212,032 B2
(45) Date of Patent: Feb. 19, 2019

(54) METHOD AND APPARATUS FOR AUTOMATICALLY INTEGRATING A MEDICAL DEVICE INTO A MEDICAL FACILITY NETWORK

(71) Applicant: CareFusion 303, Inc., San Diego, CA (US)

(72) Inventor: Robert Andrew Sobie, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 15/411,428

(22) Filed: Jan. 20, 2017

(65) Prior Publication Data

US 2017/0134221 A1 May 11, 2017

Related U.S. Application Data

(63) Continuation of application No. 12/327,614, filed on Dec. 3, 2008, now Pat. No. 9,585,562.

(51) Int. Cl.
*A61B 5/00* (2006.01)
*G06F 19/00* (2018.01)
(Continued)

(52) U.S. Cl.
CPC .......... *H04L 41/0806* (2013.01); *A47B 31/00* (2013.01); *A47B 97/00* (2013.01);
(Continued)

(58) Field of Classification Search
CPC ............. G06F 19/3406; G06F 19/3412; A61B 5/0002; H04L 67/12
See application file for complete search history.

(56) References Cited

U.S. PATENT DOCUMENTS 6,157,859 A * 12/2000 Alt ..................... A61N 1/37211
607/4
6,512,456 B1 * 1/2003 Taylor, Jr. ............. A61B 5/1112
340/539.1
(Continued)

FOREIGN PATENT DOCUMENTS

WO    WO 2006020168 A2    2/2006
WO    WO-2006035351 A2    4/2006
(Continued)

OTHER PUBLICATIONS

Chinese Reexamination Decision for Application No. 200980148587.8, dated Jun. 1, 2017, 18 pages excluding translation.
(Continued)

*Primary Examiner* — Tae K Kim
(74) *Attorney, Agent, or Firm* — Morgan, Lewis & Bockius LLP

(57) ABSTRACT

A method for integrating a medical device into a medical facility network by equipping the medical device with wireless communication device is disclosed. The medical device is provided into a medical treatment area within wireless range of the medical facility network. The medical facility network is configured to detect the medical device upon entry into the medical treatment area, and then recognize or authenticate the medical device. The medical facility network is configured to thereafter transmit an initialization signal to the medical device. A system for integrating medical devices, a medical device capable of integration, and a medical facility network are also disclosed.

18 Claims, 7 Drawing Sheets

(51) Int. Cl.
| | |
|---|---|
| *H04L 29/08* | (2006.01) |
| *H04L 12/24* | (2006.01) |
| *G16H 40/63* | (2018.01) |
| *G16H 40/20* | (2018.01) |
| *G16H 40/40* | (2018.01) |
| *A47B 31/00* | (2006.01) |
| *A47B 97/00* | (2006.01) |
| *A61G 7/05* | (2006.01) |
| *A61G 12/00* | (2006.01) |
| *H04L 29/06* | (2006.01) |
| *A61B 5/021* | (2006.01) |
| *A61B 5/03* | (2006.01) |
| *A61B 5/08* | (2006.01) |
| *A61B 5/145* | (2006.01) |

(52) U.S. Cl.
CPC ......... *A61B 5/0002* (2013.01); *A61B 5/0022* (2013.01); *A61G 7/05* (2013.01); *A61G 12/001* (2013.01); *G06F 19/00* (2013.01); *G06F 19/3418* (2013.01); *G16H 40/20* (2018.01); *G16H 40/40* (2018.01); *G16H 40/63* (2018.01); *H04L 41/12* (2013.01); *H04L 63/0876* (2013.01); *H04L 67/12* (2013.01); *A47B 2031/003* (2013.01); *A47B 2031/006* (2013.01); *A61B 5/021* (2013.01); *A61B 5/031* (2013.01); *A61B 5/0816* (2013.01); *A61B 5/14532* (2013.01); *A61B 2560/0437* (2013.01)

(56) References Cited

U.S. PATENT DOCUMENTS

| | | | | |
|---|---|---|---|---|
| 6,928,490 | B1 | 8/2005 | Bucholz et al. | |
| 7,088,233 | B2* | 8/2006 | Menard | A61B 5/0002 340/539.1 |
| 7,138,902 | B2* | 11/2006 | Menard | A61B 5/0002 340/5.53 |
| 7,384,410 | B2* | 6/2008 | Eggers | A61B 5/411 604/67 |
| 7,536,568 | B2* | 5/2009 | Price | G06F 1/26 713/300 |
| 7,698,156 | B2* | 4/2010 | Martucci | G06F 19/3462 705/3 |
| 7,788,369 | B2* | 8/2010 | McAllen | H04L 29/06 709/224 |
| 8,082,160 | B2* | 12/2011 | Collins, Jr. | G16H 40/20 705/2 |
| 8,412,361 | B1* | 4/2013 | Reynolds | A61B 17/00 700/79 |
| 2001/0016696 | A1* | 8/2001 | Bystrom | A61H 31/005 601/41 |
| 2002/0077856 | A1* | 6/2002 | Pawlikowski | G06Q 50/22 705/2 |
| 2003/0051075 | A1* | 3/2003 | Purpura | H04L 41/00 710/1 |
| 2003/0172271 | A1* | 9/2003 | Silvester | H04L 63/08 713/170 |
| 2004/0019464 | A1 | 1/2004 | Martucci et al. | |
| 2005/0043594 | A1* | 2/2005 | Dinsmoor | A61N 1/08 600/300 |
| 2005/0205439 | A1* | 9/2005 | Stafford | A61J 7/04 206/232 |
| 2005/0207534 | A1* | 9/2005 | Petrick | G01T 1/2985 378/114 |
| 2005/0256830 | A1* | 11/2005 | Siegel | G06F 19/3462 |
| 2006/0025834 | A1* | 2/2006 | Von Arx | A61N 1/08 607/60 |
| 2006/0139150 | A1* | 6/2006 | Brue | A61J 7/0481 340/309.16 |
| 2007/0008112 | A1* | 1/2007 | Covannon | A61J 3/007 340/539.12 |
| 2007/0112602 | A1 | 5/2007 | Bellon et al. | |
| 2007/0135866 | A1* | 6/2007 | Baker | A61B 5/0002 607/60 |
| 2007/0135965 | A1 | 6/2007 | Nguyen et al. | |
| 2007/0149952 | A1* | 6/2007 | Bland | G16H 50/20 604/890.1 |
| 2007/0198850 | A1* | 8/2007 | Martin | G07C 9/00087 713/186 |
| 2007/0273517 | A1* | 11/2007 | Govind | G06Q 50/24 340/572.1 |
| 2008/0109051 | A1* | 5/2008 | Splinter | A61N 1/08 607/60 |
| 2008/0154503 | A1* | 6/2008 | Wittenber | A61B 5/02055 701/300 |
| 2008/0154957 | A1* | 6/2008 | Taylor | G06F 9/4411 |
| 2008/0162185 | A1* | 7/2008 | Klabunde | G06Q 50/22 705/2 |
| 2009/0076336 | A1* | 3/2009 | Mazar | A61B 5/0402 600/300 |
| 2009/0289698 | A1* | 11/2009 | Price | G06F 1/26 327/544 |

FOREIGN PATENT DOCUMENTS

| | | |
|---|---|---|
| WO | WO 2006039059 A1 | 4/2006 |
| WO | WO-2006126107 A1 | 11/2006 |
| WO | WO 2007041843 A1 | 4/2007 |
| WO | WO-2007084807 A1 | 7/2007 |

OTHER PUBLICATIONS

Korean Notice of Allowance for Application No. 2016-7023311, dated Apr. 20, 2017, 2 pages excluding translation.
Chinese Office Action for Application No. 200980148587.8, dated Feb. 3, 2016, 8 pages (excluding translation).
Australian Examination Report No. 1 for Application No. 2009322563, dated Jun. 22, 2015, 3 pages.
Canadian Office Action for Application No. 2745272, dated Dec. 7, 2015, 6 pages.
Korean Office Action for Application No. 10-2011-7013696, dated Dec. 8, 2015, 7 pages (excluding translation).
Chinese Office Action in Chinese Patent Application No. 20090148587.8 dated Nov. 15, 2014, 9pages (including English summary).
Communication pursuant to Article 94(3) EPC in European Patent Application No. 09761135.4 dated Jul. 7, 2014, 8 pages.
Russian Official Decision of Rejection in Russian Patent Application No. 2011124946 dated Sep. 12, 2014, 13 pages (including English translation).
4th Mexican Office Action in Mexican Patent Application No. MX/a/2011/005614, 3 pages.
Japanese Office Action in Japanese Patent Application No. 2011-539619 date unknown, 3 pages (translation unavailable).
Russian Official Decision of Rejection in Russian Patent Application No. 201124946 dated Jan. 9, 2014, 13 pages (including English translation).
International Search Report from related PCT Application No. PCT/US20069/066140, dated Mar. 2, 2010.
Korean Office Action for Application No. 2016-7023311, dated Nov. 4, 2016, 6 pages excluding English translation.
Canadian Office Action for Application No. 2745272, dated Dec. 28, 2016, 6 pages.
Chinese Reexamination Notice for Application No. 200980148587. 8, dated Nov. 28, 2016, 19 pages excluding translation.
European Office Action for Application No. 09761135.4, dated Oct. 17, 2017, 3 pages.
European Office Action for Application No. 09761135.4, dated Nov. 15, 2018, 5 pages.
Indian Office Action for Application No. 3669/CHENP/2011, dated Sep. 27, 2018, 6 pages.

* cited by examiner

METHOD AND APPARATUS FOR AUTOMATICALLY INTEGRATING A MEDICAL DEVICE INTO A MEDICAL FACILITY NETWORK

RELATED APPLICATIONS

This application is a continuation of U.S. patent application Ser. No. 12/327,614, filed on Dec. 3, 2008, issued as U.S. Pat. No. 9,585,562 on Mar. 7, 2017, which is incorporated in its entirety herein by reference.

FIELD

The present disclosure relates to a method and apparatus for automatically integrating a medical device into a medical facility network.

BACKGROUND

In modern medical facilities such as hospitals, health care professionals use various medical devices to view patient information or provide medical care to a patient. Some medical devices administer medical care; for example, an intravenous (IV) pump that delivers a solution containing a medication into a patient's bloodstream or a ventilator that delivers oxygen to a patient's lungs. Other medical devices measure and report a patient's physiological status; for example, an electrocardiograph (EKG) that measures and records electrical currents associated with heart contractions.

In a patient room, typically the patient is lying in a bed surrounded by various medical devices. In some cases, the medical devices are awkwardly and dangerously arranged around the patient's bed. The medical devices may hang from the ceiling, hang from bed rails, lie on the bed, sit on the floor, etc. The placement of these medical devices is often random and creates serious safety risks to the patient. There are also risks to health care professionals who attempt to carry or maneuver heavy devices in crowded quarters.

These medical devices have cords, wires, and tubes arranged in a tangled web that poses a safety risk. Also, many medical devices have their own display panel and control panel, which may be small (difficult to see), awkwardly located, space occupying, expensive, and redundant. Many medical devices include their own battery, which in addition to the extra control panels and read-out screens, takes up space and adds weight and expense. In certain rooms such as an intensive care unit, efficient organization of medical devices and utilization of space are even more critical due to the unstable, critical condition of the patient, number of devices, and the high cost of space.

Generally, the various medical devices surrounding a patient's bed operate independently of each other and include non-standard wires, tubes, and interfaces. One problem is lack of integration between the medical devices. For example, some medical devices generate information in a proprietary format, which is not compatible with other medical devices from different vendors. In another example, a medical device may produce an analog signal for a patient's vital signs. Because the signal is not digital or recorded, the analog signal must be transcribed onto a piece of paper or else the information is lost. As a result of this lack of integration, health care professionals must pay greater attention to control and monitor many medical devices individually, requiring more personnel to transcribe the data, more time to review the data, and greater potential for lost data and transcription error. Some devices with analog signals may store the data for short periods of time but again, the time must be taken later to review and transcribe the information.

Another problem is that many of the sophisticated medical devices need to boot up and/or power up before they can be used, normally requiring a certain amount of time before the medical devices are operable and integrated into the network. In emergency situations, time is critical and any delay can cause complications for a patient. It would be desirable for the medical devices to be ready for operation at the time a health care professional brings the medical devices into a patient room. In addition to patient rooms, these same concerns apply for operating rooms and other treatment rooms, including emergency rooms, examination rooms, etc.

Additionally, many medical devices operate independent of a health care computer system or an electronic medical record in which a database of patient medical records is stored. Consequently, health care personnel need to read information from the medical devices and manually enter the information into the health care computer system for storage in the database. In one example, data from medical devices such as glucometers, electrocardiogram (EKG) apparatuses, IV pumps, blood pressure monitoring, ventilators, and respiratory devices are not linked to the electronic medical record. Manual transfer of information from the medical devices to the health care computer system is time-consuming and prone to error.

The aforementioned problems and inefficiencies with medical devices are of particular concern in intensive care units for neonates, children, and adults. In these environments, the patients are typically at higher risk; consequently, there is a greater volume of information per patient and a greater number of medical devices used. Therefore, there is an even greater need to have an efficient system which integrates the initialization and control of the medical devices.

SUMMARY

The presently disclosed embodiments are directed to solving one or more of the problems presented in the prior art, described above, as well as providing additional features that will become readily apparent by reference to the following detailed description when taken in conjunction with the accompanying drawings.

One or more embodiments are directed to a method of initializing a medical device within a medical treatment area. The method includes detecting the medical device upon introduction of the medical device into the medical treatment area within a wireless range of a medical facility network and authenticating the medical device based on device identity information specific to the medical device if the medical device is not recognized by the medical facility network. The method also includes transmitting an initialization signal from the medical facility network to the medical device if the medical device is recognized or authenticated by the medical facility network. The method further includes initializing the medical device in response to the medical device receiving the initialization signal, wherein initializing comprises one of powering the medical device into an active power state, starting up the software program, and unlocking the medical device.

One or more embodiments are directed to a system for integrating a medical device into a medical facility network. The system includes a terminal interfacing with the medical facility network, a display in communication with the terminal, and a medical device within wireless range of the medical facility network. The medical facility network is configured to detect the medical device upon introduction of the medical device into a medical treatment area, determine if the detected medical device is recognized, authenticate the medical device based on device identity information specific to the medical device if the medical device is not recognized, and transmit an initialization signal to the medical device if the medical device is recognized or authenticated. In response to receiving the transmitted initialization signal, the medical device is configured to initialize by one of powering the medical device into an active power state, starting up a software program, and unlocking the medical device.

One or more embodiments are directed to a medical device having a processor, a storage medium and a wireless communication interface. The medical device is configured to be automatically detected upon introduction into a medical treatment area, recognized or authenticated by a medical facility network, the authentication based on device identity information specific to the medical device if the medical device is not recognized, and automatically initialized, in response to receiving an initialization signal, the automatic initialization comprising one of powering the medical device into an active power state, starting up a software program, and unlocking the medical device.

The present invention is not limited to the aforementioned embodiments, and other features of the embodiments will become apparent after review of the hereinafter set forth Brief Description of the Drawings, Detailed Description, and the Claims, or may be learned by practice of the invention.

BRIEF DESCRIPTION OF THE DRAWINGS

The foregoing aspects of the embodiments described herein will become more readily apparent by reference to the following detailed description when taken in conjunction with the accompanying drawings wherein.

DETAILED DESCRIPTION

Figure 1:
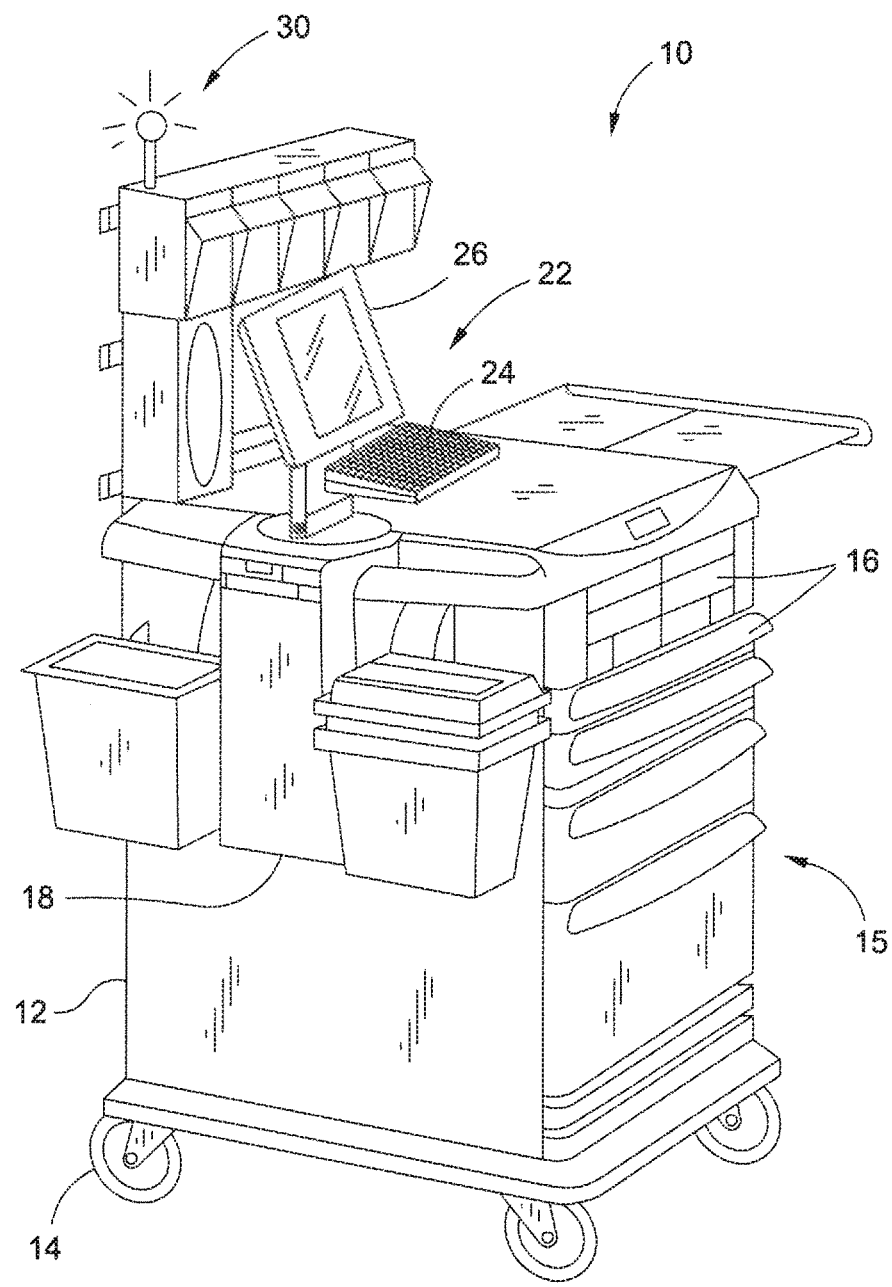
FIG. 1 is a perspective depiction of an exemplary medical device, according to disclosed embodiments.

Reference will now be made in detail to the presently disclosed embodiments, examples of which are illustrated in the accompanying drawings, wherein like reference numerals refer to like elements throughout.

The present invention addresses the need to integrate medical devices in a medical facility. The integration of medical devices allows a health care professional to view the medical devices operating conditions on a display and control the medical devices from a single terminal. Integration of the medical devices is facilitated by the use of wireless communication.

Referring initially to FIG. 1, a medical device 10 in accordance with certain embodiments is shown. Medical device 10 may comprise a mobile or stationary dispensing station 15. Dispensing station 15 may be used in an institution to controllably dispense medication and other items for use in treating patients. Such an exemplary medical device 10 is described in U.S. Patent Application Publication No. 20070135965, entitled "System and Method for Storing Items and Tracking Item Usage," incorporated by reference in its entirety. However, the dispensing station 15 is but one example of a medical device 10 for purposes of this disclosure. The term "medical device" as used herein refers to any device capable of wireless communication, such as dispensing station 15, an infusion pump, an oxygen monitor, etc., that is configured for wireless communication.

As shown in FIG. 1, the dispensing station 15 comprises a cabinet 12 supported by wheels 14 so that it may be moved easily to medical treatment areas throughout a medical facility, such as into an operating room. In the exemplary embodiment shown, the cabinet 12 holds sliding trays or drawers 16 of varying shapes and sizes for storing a wide variety of items. The number and configuration of the drawers 16 may be modified to meet the needs of the institution in which the dispensing station 15 is used.

Reference numeral 30 refers to a schematically depicted a wireless communication device that provides wireless communication capability to the medical device 10. The depiction is representational only, and is not meant to depict any actual physical configuration or location of any particular wireless communication device.

Figure 2:
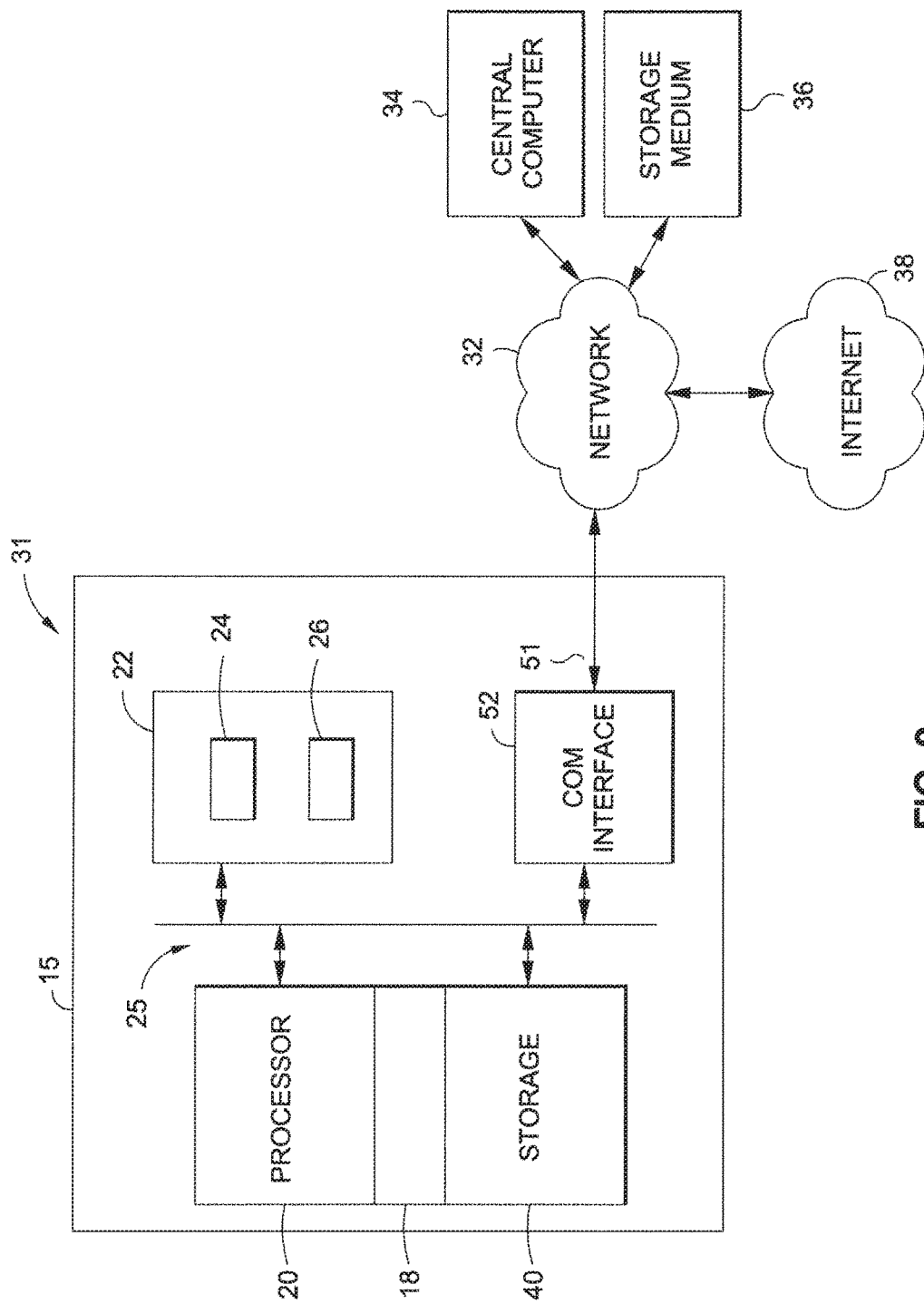
FIG. 2 is a block diagram of an exemplary operating system of the medical device of FIG. 1 and shows a network connection between the medical device, a central computer, a storage medium, and the internet according to disclosed embodiments.

Referring now to FIG. 2, in some embodiments, drawers 16 are coupled to a control unit 18 for limiting and tracking user access to stored items. The control unit 18 comprises a slide control mechanism (not shown) with locking hardware, such as solenoids, latches, and/or muscle wires, controlled by a processor 20. The control unit 18 also includes a storage medium 40 in communication with processor 20. In some embodiments, the processor 20 is in communication with a device interface such as a terminal 22. In some embodiments the communication between the processor 20 and storage medium 40 or terminal 22 is achieved using a bus 25.

The terminal 22 comprises a keyboard 24 and a display screen or display 26. In some embodiments, display 26 is a touch screen, which allows a health care professional or user to interact with images displayed on the screen to input data and commands for use by the processor 20 to control the operation of the cabinet 12. Persons of ordinary skill in the art will appreciate that a mouse or other pointing device (not shown) may be used in combination with display 26 to interact with images displayed on the screen.

In one embodiment, a communication interface 52 is also in communication with processor 20 and terminal 22 via bus 25. Communication interface 52 may comprise a network interface card, modem, port, or some other communication device. In one embodiment, the communication interface 52 is coupled to and communicates with a medical facility network 32 via communications link 51. In some embodiments, communication interface 52 is in wireless communication with medical facility network 32. This may include incorporation of or connection to a wireless communication device 30 (not illustrated in FIG. 2).

Figure 3:
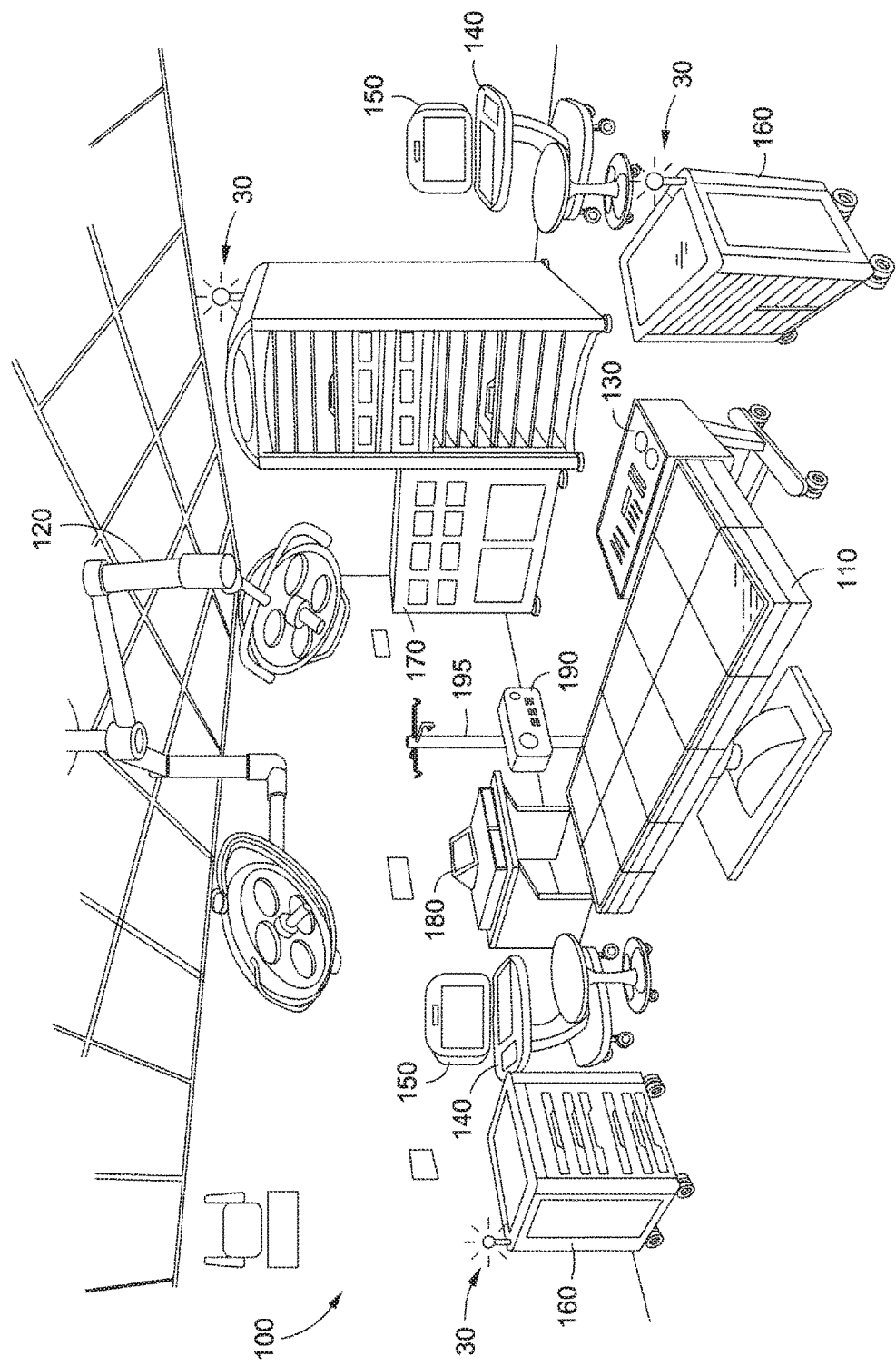
FIG. 3 is a perspective depiction of an exemplary medical treatment area, such as an operating room, in which the disclosed embodiments may be employed.

Referring briefly now to FIG. 3, a perspective depiction of an exemplary operating room 100, in which a medical device 10 may be employed is shown. It is noted that the disclosed embodiments are not limited to an operating room 100, and may be utilized in accordance with any medical treatment area within a medical facility, including, for example, a patient room.

In the exemplary embodiment depicted in FIG. 3, an operating room 100 includes a patient bed 110, a lighting assembly 120, a utensil platform 130, a plurality of terminals 140, a plurality of displays 150, a plurality of inventory storage devices 160, a waste disposal device 170, an electronic monitoring device 180, an IV fluid stand 195 and an infusion pump 190. Operating room 100 may additionally include other equipment as desired, including, for example, anesthesia equipment, defibrillators, vital signs monitors, respiratory ventilators, dialysis machines, etc.

Figure 4:
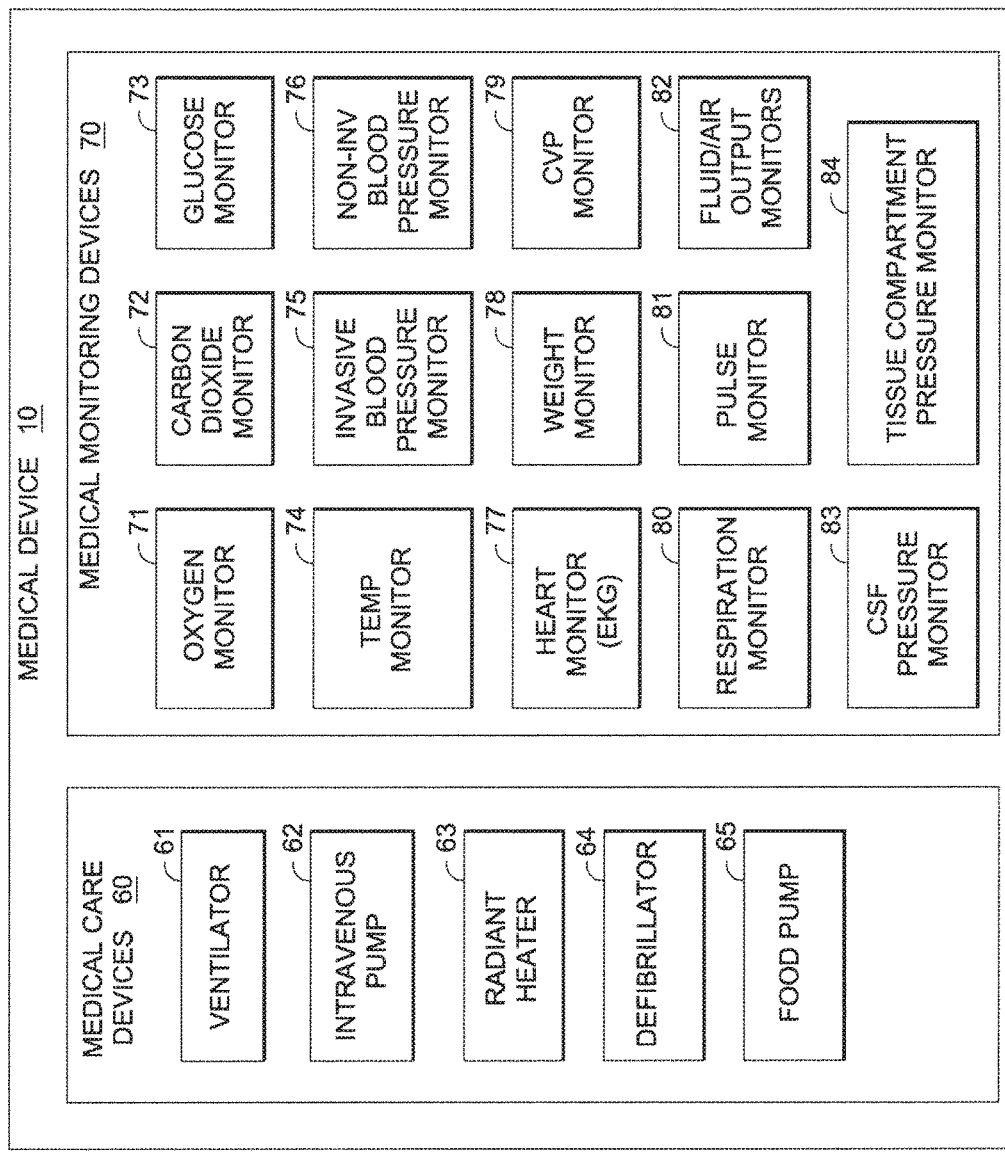
FIG. 4 is a block diagram of exemplary medical devices which may be used according to disclosed embodiments.

As stated above, "medical device" 10 refers to any device capable of wireless communication, such as dispensing station 15 or inventory storage device 160. Exemplary additional equipment which may be referred to as medical devices 10 are shown in FIG. 4. Such medical devices 10 include, for example, medical care devices 60 and medical monitoring devices 70. Medical care devices 60 include a ventilator 61, an IV pump 62, an radiant heater 63, a defibrillator 64, dispensing station 15, inventory storage device 160, etc. Medical monitoring devices 70 include an oxygen monitor 71, a carbon monoxide monitor 72, a glucose monitor 73, a temperature monitor 74, an invasive blood pressure monitor 75, a non-invasive blood pressure monitor 76, a heart monitor (EKG) 77, a weight monitor 78, a central venous pressure (CVP) monitor 79, a respiration monitor 80, a pulse monitor 81, a fluid/air output monitor 82, a cerebrospinal fluid (CSF) monitor 83, and a tissue compartment pressure monitor 84. Both medical care devices 60 and medical monitoring devices 70 are meant to be exemplary and not an exhaustive list of medical devices 10 for use in the present invention.

It should be apparent that medical devices 10 may be transported and used for a number of patients in a number of medical treatment areas. As a result, these medical devices 10 are frequently cycled on and off. Because many health care professionals handle the medical devices 10, it may be difficult to ascertain the location or track the movement of the medical devices 10 within the medical facility.

Consequently, equipping the medical devices 10 with the ability to expedite their deployment within an operating room 100 is desirable. In accordance with certain exemplary embodiments, medical devices 10 such as dispensing station 15 or inventory storage device 160 include wireless communication device 30. Without being bound by any particular theory, it is believed that equipping the medical devices 10 with wireless communication device 30 will reduce the time necessary to integrate the medical devices 10 into an operating room 100 or other medical treatment area and initialize the medical devices 10.

Referring back to FIG. 2, in certain embodiments the dispensing station 15 is part of a system 31 and is linked via a medical facility network 32 to a central computer 34 with access to a centralized storage device such as storage medium 36. The devices in communication with medical facility network 32 may also be referred to as entities or nodes. The arrangement of the network 32 and the nodes may take different forms, and that depicted in FIG. 2 is exemplary only.

In certain embodiments, medical facility network 32 is configured to be able to physically connect to the medical devices 10 and wirelessly connect to the medical devices 10. Technologies suitable for wireless communication include Bluetooth, Zigbee, radio frequency identification (RFID) and ultra-wide band (UWB), to name a few. In one embodiment, communication interface 52 comprises a wireless network interface card.

Connection of medical facility network 32 to the medical devices 10 allows the medical devices 10 to share and exchange data with other medical devices 10 and entities such as central computer 34 and storage medium 36. Storage medium 36 may include, for example, one or more databases having patient-specific information and information regarding items currently stored or are to be stored in the dispensing station 15. In these embodiments, the medical facility network 32 provides the means for the control unit 18 to automatically obtain patient-specific information. In certain exemplary embodiments, medical facility network 32 is connected to the Internet 38.

Because medical facilities employ a very large number of different medical devices 10, it is desirable to limit the wireless range of the medical devices 10, so as to limit interference between the medical devices 10 and other equipment. In a preferred embodiment, the wireless range of the medical devices 10 is limited to approximately the medical treatment area. Such a limit on the wireless range may be achieved by limiting the power level of the medical device 10 to a maximum threshold value.

Alternatively, rather than limiting the wireless range of the medical devices 10, employing physical or electromagnetic barriers that prevent the transmitting and receiving of wireless communication signals outside of the desired area may be used. For example, in a typical operating room 100, the walls may be lined with lead, thereby preventing transmission of wireless communication signals into and out of the room.

In should be appreciated that the medical devices 10 may be secure or unsecure in their connection 51 to medical facility network 32. However, it is desirable for the medical devices 10 and the medical facility network to be in compliance with the Health Insurance Portability & Accountability Act of 1996 (HIPAA) and other relevant standards.

In certain aspects, medical facility network 32 comprises a facility-wide network. In certain other aspects, medical facility network 32 comprises a local network. A local network may include, for example, a network that is dedicated to a single room.

Figure 5:
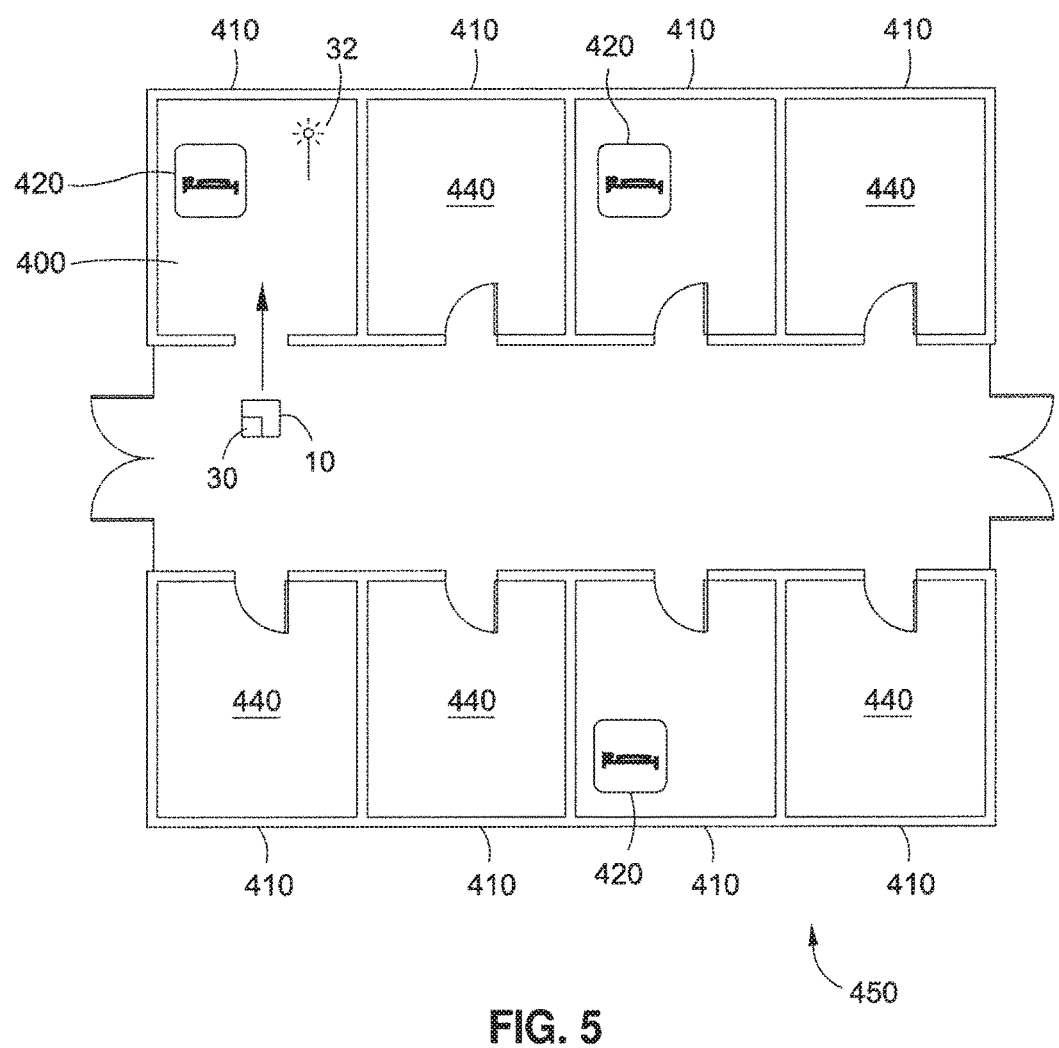
FIG. 5 is a schematic depiction of a medical device entering a medical treatment area, according to disclosed embodiments.

Referring now to FIG. 5, a schematic depiction of a medical device 10 entering a medical treatment area 400 is shown. In certain embodiments, medical treatment area 400 comprises a patient room 410 in a medical facility 450. The medical treatment area 400 could also be an operating room, an examination room, etc., as explained earlier.

As shown in FIG. 5, a plurality of patient rooms 410 may be part of medical facility 450. Patient rooms 410 may be occupied by patients 420 or may be vacant 440. In certain embodiments, medical device 10 and medical treatment area 400 both have wireless communication devices 30 allowing wireless interaction. In certain embodiments, the wireless communication device 30 of medical treatment area 400 is connected to medical facility network 32.

As medical device 10 enters through wireless communication devices 30 treatment area 400, medical facility network 32 detects the presence of medical device 10. In certain embodiments, medical facility network 32 transmits an initialization signal to medical device 10. The exchange of this information will be further described in detail with reference to FIGS. 6-7.

In medical facilities 450 such as hospitals, having a large number of sophisticated medical devices 10 at any time, integration of such medical devices 10 into an overarching medical facility network 32 has become a necessity. This necessity has been caused in part due to the interdependence of certain medical devices 10 with each other. For example, a patient 420 connected to an IV pump 62 and a heart monitor (EKG) 77 may require the IV pump 62 to adjust its drip rate in response to a particular heart rate as detected by heart monitor 77. This simple example illustrates the interdependence of just two medical devices 10. It should be appreciated that many medical devices 10 are dependent on other medical devices 10, thereby compounding the need for integration.

Figure 6:
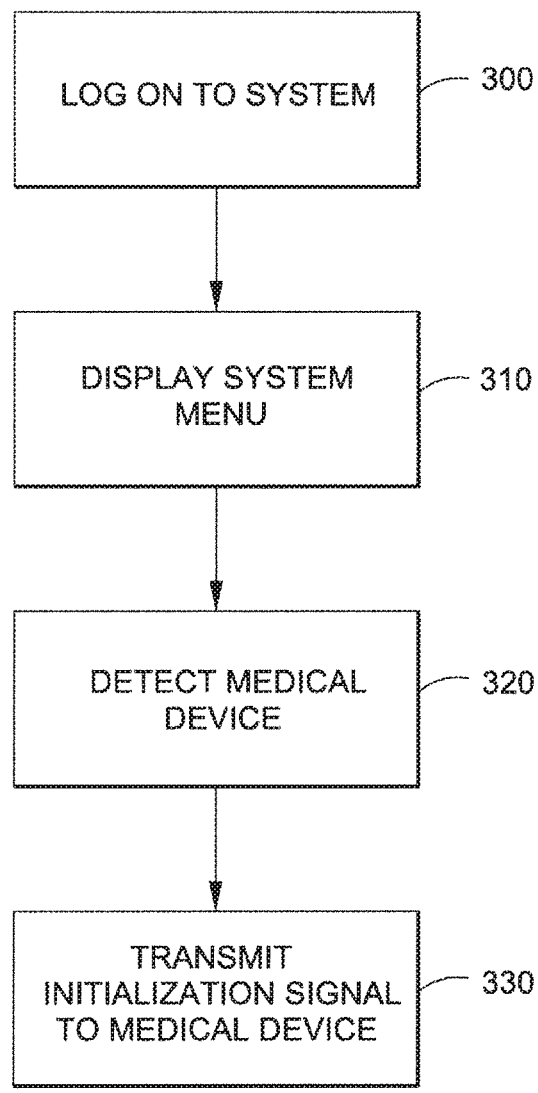
FIG. 6 is a flow diagram illustrating a method of integrating a medical device into a medical facility network, according to disclosed embodiments.

Referring now to FIG. 6, a flow diagram illustrating a method of integrating a medical device 10 into a medical facility network 32, according to disclosed embodiments is shown. Initially, at step 300 of the flow diagram, a user logs on to access a software application by entering a personal identifier and password via a terminal 140 located within medical treatment area 400. If the terminal 140 identifies the user as having the appropriate authority, a system menu is displayed on display 150 at step 310. In an exemplary embodiment, the software application is associated with patient records. According to a preferred embodiment, the system menu is a comprehensive menu, allowing a user access patient records, manage inventory and perform billing functions.

Once the user is able to view the system menu, if a medical device 10 having wireless capability 30 enters the medical treatment area 400, medical facility network 32 automatically detects the medical device 10 at step 320. Such detection is achieved by either the medical device 10 transmitting a signal to make medical facility network 32 aware that the medical device 10 is within wireless range or by medical facility network 32 periodically transmitting signals and receiving responses from medical devices 10 that are within wireless range.

After the medical device 10 has been detected, medical facility network 32 transmits an initialization signal to the medical device at step 330. The initialization signal may comprise instructions to power up to an active power state. As stated above, the medical devices 10 are frequently transported and used for a number of patients 420 in a number of medical treatment areas 400. Therefore, the power state of the medical device 10 is an unknown. Typically, the medical device 10 is in a low power, sleep or off state when not being actively used in another medical treatment area 400.

Alternatively, the initialization signal may comprise instructions to begin start up of a software program. For example, in certain embodiments, the medical device 10 has software installed for running a specific program or set of programs. Such is the case for many sophisticated medical devices 10, such as infusion pump 190, for example. In such an embodiment, infusion pump 190, may begin running through pre-operation housekeeping checks.

Alternatively, the initialization signal may comprise instructions to cause the medical device 10 to assume a start up position. For example, the initialization signal may cause the medical device 10 to unlock. This initialization would be particularly useful for medical devices 10 such as dispensing station 15, which typically has its drawers 16 locked due to the contents within the drawers 16, e.g., medications.

It should be realized that by integrating medical devices 10 into a system 31 linked to medical facility network 32, a plurality of medical devices 10 may be controlled, e.g., initialized, at a single terminal 140. Consequently, medical device information such as operating conditions may be viewed by a user on a single display 150 or multiple displays 150 arranged throughout medical treatment area 400.

Figure 7:
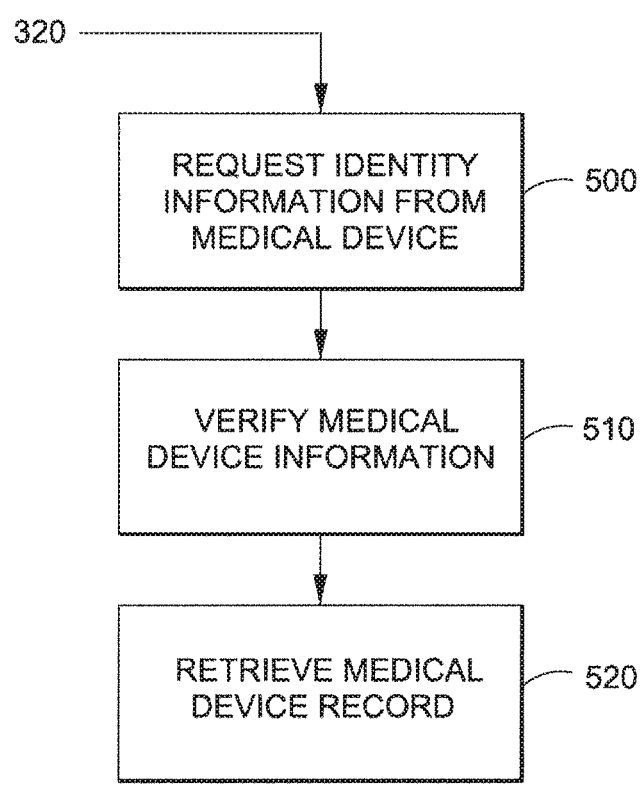
FIG. 7 is a flow diagram illustrating a method of authenticating a medical device by a medical facility network, according to disclosed embodiments.

Referring now to FIG. 7, a flow diagram illustrating a method of authenticating a medical device 10 by a medical facility network 32, according to disclosed embodiments is shown. As a safeguard against initializing medical devices 10 which are not recognized by the medical facility 450 for a variety of reasons, medical facility network 32 may authenticate a medical device 10 after detecting medical device 10 at step 320. Some reasons medical facility network 32 may not recognize a medical device 10 include, for example, the medical device 10 is new and has not yet been entered into the network 32, the medical device 10 is retired and has been removed from the network 32, or the medical device 10 is already dedicated to another patient 420 and requires a discharge from the patient 420 before it can be initialized for a new patient 420.

For authentication, medical facility network 32 requests identity information from a medical device 10 at step 500. Such request may be accomplished by medical facility network 32 transmitting a request signal to the medical device 10. This occurs after the medical device 10 has been powered up, as in FIG. 6.

In response to the information, the medical device 10 transmits a signal to medical facility network 32 comprising the requested device identity information. In certain embodiments, the device identity information comprises an electronic serial number associated with the medical device 10. In certain embodiments, other device identifiers may be used.

Once medical facility network 32 receives medical device identity information, it can verify the authenticity of the medical device 10 at step 510. Verification of the authenticity may be achieved, for example, by the medical facility network 32 inquiring as to whether a record exists for the medical device 10. The medical device record may be stored in storage medium 36 or the medical device 10 itself.

After the medical device 10 is authenticated, the medical facility network 32 may then retrieve the medical device record from storage medium 36 or the medical device 10 at step 520. The medical device record may then be displayed on display 150 so that a user can view and edit the medical device record at terminal 140.

During the authentication of the medical device 10, a user may choose at any time to forgo transmitting an initialization signal to the medical device 10 at step 330. Possible reasons for not sending an initialization signal include the medical device 10 is not the right type, the medical device 10 is no longer needed, etc.

Embodiments disclosed herein provide a method and system for integrating a medical device 10 within a medical treatment area 400. According to certain embodiments disclosed herein, the medical device 10 to be integrated is equipped with a wireless communication device 30 such as by attaching or incorporating a Bluetooth or other wireless device into the medical device 10. The wireless communication device 30 is relatively inexpensive and may be readily installed. The medical devices 10 may then communicate with the medical facility network 32 wirelessly. Such wireless communication allows for the medical devices 10 to be initialized upon entry into a medical treatment area 400.

Connection of medical devices 10 with medical facility network 32, which in turn is in communication with a user terminal 140, allows a user to control the operating conditions of a plurality of medical devices 10 from a single terminal 140. Such integration of medical devices 10 promotes medical facility 450 efficiency and improves patient care.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of initializing a medical device within a medical treatment area, comprising:
   detecting the medical device upon introduction of the medical device into the medical treatment area within a wireless range of a medical facility network;
   authenticating the medical device based on device identity information specific to the medical device if the medical device is not recognized by the medical facility network;
   transmitting an initialization signal from the medical facility network to the medical device if the medical device is recognized or authenticated by the medical facility network;
   initializing the medical device in response to the medical device receiving the initialization signal, wherein initializing comprises one of powering the medical device into an active power state, starting up the software program, and unlocking the medical device; and
   preventing transmission of the initialization signal from the medical facility network to the medical device based on a user request to forgo transmission of the initialization signal during the authenticating of the medical device.

2. The method of claim 1, wherein after detection of the medical device, the medical facility network transmits an identity information request signal to the medical device.

3. The method of claim 2, wherein in response to the identity information request signal, the medical device transmits an identity information signal to the medical facility network.

4. The method of claim 1, wherein the medical facility network is connected to the internet.

5. The method of claim 1, wherein the wireless range is limited to approximately the medical treatment area.

6. The method of claim 1, wherein the medical facility network comprises a local network or facility-wide network.

7. The method of claim 1, wherein the device identity information specific to the medical device is an electronic serial number.

8. The method of claim 1, wherein the medical device is not recognized by the medical facility network because the medical device is new and has not yet been entered into the medical facility network.

9. The method of claim 1, further comprising preventing transmission of the one or more initialization signals from the medical facility network to the medical device based on user input during the authenticating the medical device.

10. A system for integrating a medical device into a medical facility network, comprising:
    a terminal interfacing with the medical facility network;
    a display in communication with the terminal; and
    a medical device within wireless range of the medical facility network, wherein the medical facility network is configured to:
    detect the medical device upon introduction of the medical device into a medical treatment area;
    determine if the detected medical device is recognized;
    authenticate the medical device based on device identity information specific to the medical device if the medical device is not recognized;
    transmit an initialization signal to the medical device if the medical device is recognized or authenticated; and
    prevent transmission of the one or more initialization signals from the medical facility network to the medical device based on a user request to forgo transmission of the one or more initialization signals during the authenticating of the medical device,
    wherein, in response to receiving the transmitted initialization signal, the medical device is configured to initialize by one of powering the medical device into an active power state, starting up a software program, and unlocking the medical device.

11. The system of claim 10, wherein the medical facility network is connected to the internet, thereby facilitating data exchange between the medical facility network and another entity.

12. The system of claim 10, wherein the wireless range is limited to approximately the medical treatment area.

13. The system of claim 10, wherein the medical facility network comprises a local network or facility wide network.

14. A medical device comprising:
    a processor;
    a storage medium; and
    a wireless communication interface, wherein the medical device is configured to be:
    automatically detected upon introduction into a medical treatment area;
    recognized or authenticated by a medical facility network, the authentication based on device identity information specific to the medical device if the medical device is not recognized;
    automatically initialized, in response to receiving an initialization signal, the automatic initialization comprising one of powering the medical device into an active power state, starting up a software program, and unlocking the medical device; and
    prevented from receiving the initialization signal based on a user request to forgo transmission of the initialization signal during the authenticating of the medical device.

15. The method of claim 14, wherein the medical device is further configured to transmit an identity information signal to the medical facility network in response to receiving an identity information request signal.

16. The medical device of claim 14, wherein the device identity information specific to the medical device is an electronic serial number.

17. The medical device of claim 14, wherein the medical device is new and has not yet been entered into the medical facility network, causing the medical device to not be recognized by the medical facility network.

18. The medical device of claim 14, wherein the medical device is retired and has been removed from the medical facility network, causing the medical device to not be recognized by the medical facility network.

* * * * *

UNITED STATES PATENT AND TRADEMARK OFFICE
CERTIFICATE OF CORRECTION

PATENT NO. : 10,212,032 B2
APPLICATION NO. : 15/411428
DATED : February 19, 2019
INVENTOR(S) : Robert Andrew Sobie Page 1 of 1

It is certified that error appears in the above-identified patent and that said Letters Patent is hereby corrected as shown below:

In the Claims
Column 10, Line 55, replace "method of claim 14" with --medical device of claim 14--

Signed and Sealed this
Seventeenth Day of September, 2019

Andrei Iancu
*Director of the United States Patent and Trademark Office*